United States Patent [19]

Suda

[11] Patent Number: 5,250,259

[45] Date of Patent: Oct. 5, 1993

[54] CHEMILUMINESCENT DETECTOR

[75] Inventor: Masayuki Suda, Tokyo, Japan

[73] Assignee: Seiko Instruments Inc., Japan

[21] Appl. No.: 869,524

[22] Filed: Apr. 15, 1992

[30] Foreign Application Priority Data

Apr. 17, 1991 [JP] Japan ................... 3-85593

[51] Int. Cl.$^5$ ........................... G01N 21/76
[52] U.S. Cl. ........................... 422/52; 422/55;
422/58; 422/82.05; 436/172; 356/36; 362/34;
250/361 C; 435/291
[58] Field of Search ............. 422/52, 55, 58, 82.05;
436/172, 805; 356/36, 394; 362/34; 250/361 C;
435/291

[56] References Cited

U.S. PATENT DOCUMENTS 4,672,039 6/1987 Lindblom ..................... 435/291
5,128,102 7/1992 Kaneko et al. ................ 422/56

*Primary Examiner*—James C. Housel
*Assistant Examiner*—David Redding
*Attorney, Agent, or Firm*—Bruce L. Adams; Van C. Wilks

[57] ABSTRACT

A chemiluminescent detector is formed on a single crystal silicon substrate. A reaction unit is formed on and integral with a substrate. The reaction unit is for mixing a test sample with a chemiluminescent reagent and is formed on the substrate by anisotropic etching. The reaction unit includes a plurality of through-holes interconnected with grooves formed in the substrate. A detection unit, including a silicon photodetector, is also formed on and integral with the substrate and detects chemiluminescent light generated by a chemiluminescent reaction between the test sample and the chemiluminescent reagent. Introducing ports introduce the test sample and the chemiluminescent reagent into the reaction unit. A pair of glass plates sandwich the substrate.

14 Claims, 2 Drawing Sheets

FIG. 1
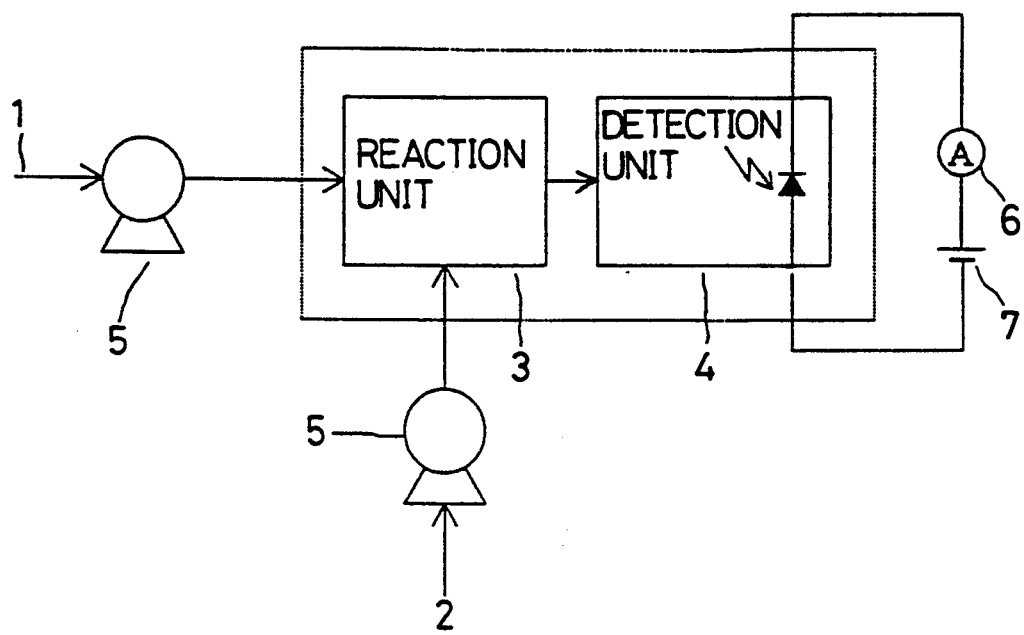
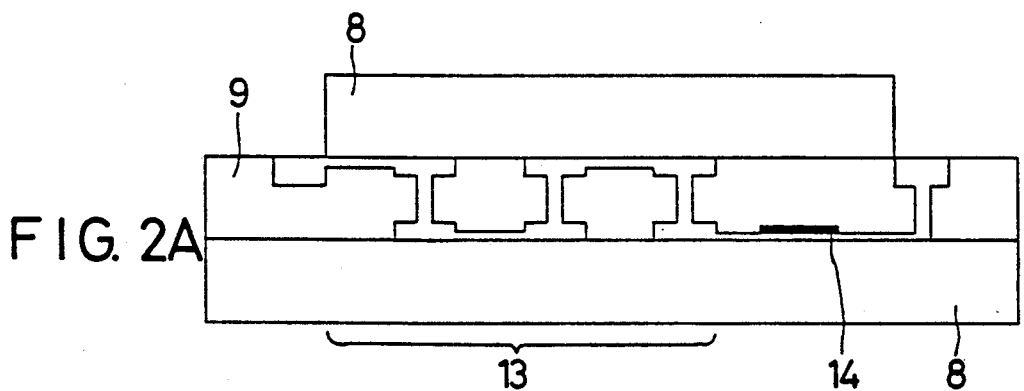
FIG. 2A
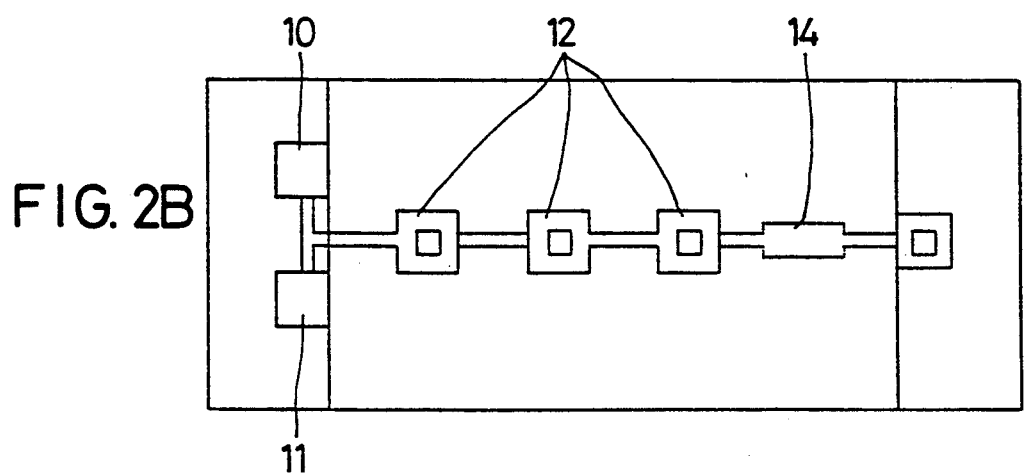
FIG. 2B

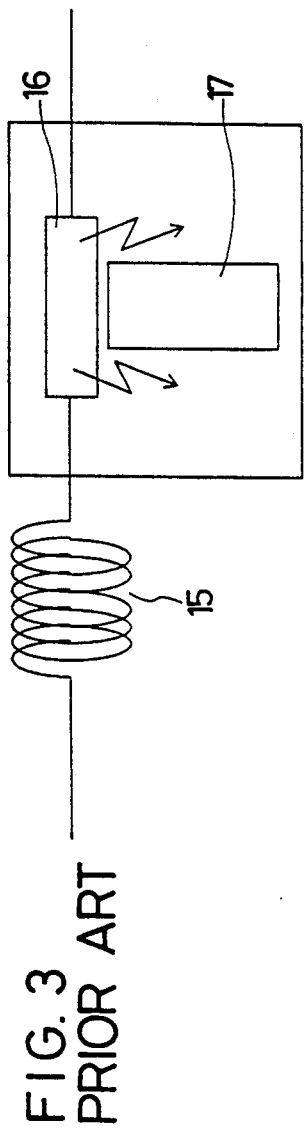
FIG. 3
PRIOR ART
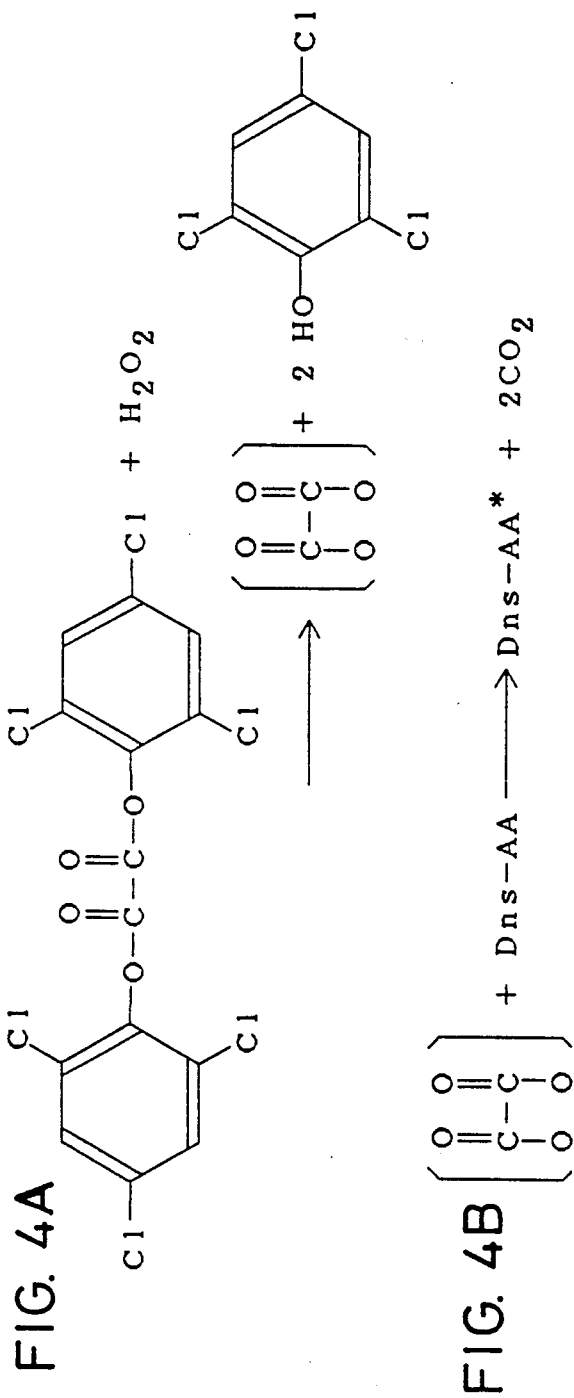
FIG. 4A
FIG. 4B
FIG. 4C

CHEMILUMINESCENT DETECTOR

BACKGROUND OF THE INVENTION

This invention relates to an apparatus for effecting quantitative and qualitative analyses on the basis of chemiluminescence in medial science, pharmacology, chemical analysis and foodstuff industry.

A conventional chemiluminescent detector comprises a reaction coil 15 for mixing a chemiluminescent reagent and a test sample and inducing a luminous reaction, a flow cell 16 which is a portion for actually detecting luminescence, and a photoelectric tube 17 for converting an optical signal to an electric signal, as shown in FIG. 3. The reaction coil 15 and the flow cell 16 are separate components and are connected by a stainless steel tube.

However, in the conventional chemiluminescent detector as mentioned above, the reaction unit and the detection unit are separate components and are connected by piping. Therefore, since chemiluminescence occurring in the reaction unit attenuates while the test sample is transferred to the detection unit it is very difficult to detect very weak luminescent. Moreover, a machining process is necessary for the production of the reaction unit and the detection unit, there is a limitation to miniaturization and a very small quantity of a test sample of a nano-liter order cannot be handled. Another problem is that the cost of production is high because precision machining is necessary.

SUMMARY OF THE INVENTION

It is an object of the present invention to provide a chemiluminescent detector which has an integral structure of the reaction unit and the detection unit. The inventive chemiluminescent detector can handle a very small quantity of test sample and is economical to fabricate.

In accordance with the present invention a reaction unit and a detection unit are formed on the same substrate in a chemiluminescent detector. The and minimizes the distance from the reaction unit to the detection unit is thus minimized so as to minimize the attenuation of luminescence. Since the reaction unit is produced by anisotropic etching of a silicon substrate and not by a machining process, miniaturization can be made easily and a construction for handling a very small quantity of test sample can be accomplished economically. Furthermore, a photodiode structure fabricated on the silicon substrate is used as a part of the detection unit.

In the chemiluminescent detector constituted as described above, a test sample and a chemiluminescent reagent are mixed in the reaction unit for causing a chemiluminescent reaction, and a specific substance in the test sample and the chemiluminescent reagent react with each other and generate light having a specific wavelength. The mixed liquid is then sent to the detection unit and the intensity of the light is converted by the photodiode to the amplitude of an electric signal (current value).

BRIEF DESCRIPTION OF THE DRAWINGS

FIG. 1 is a schematic view of a chemiluminescent detector of the present invention;

FIGS. 2A and 2B show an embodiment of the chemiluminescent detector of the present invention, wherein FIG. 2A is a longitudinal sectional view and FIG. 2B is plan view;

FIG. 3 is a schematic view of a conventional chemiluminescent detector; and

FIGS. 4A to 4C are reaction formulae of the luminescence reaction of a dansylamino acid.

DETAILED DESCRIPTION OF THE PREFERRED EMBODIMENT

Hereinafter, an embodiment of the present invention will be explained with reference to the drawings.

In FIG. 1, a test sample 1 and a chemiluminescent reagent 2 are sent by pumps 5 to a reaction unit 3. The test sample 1 and the chemiluminescent reagent 2 are mixed in the reaction unit 3 and a chemiluminescent reaction takes place. Thereafter, the mixed liquid moves to a detection unit 4. The detection unit 4 comprises a silicon photodiode, and an ammeter 6 and a D.C. power supply 7 are connected to the detection unit 4. When light does not irradiate the photodiode, no current flows through the ammeter 6 because a voltage in a reverse direction is applied to the photodiode. On the other hand, when light irradiates on the photodiode, a current flows through the ammeter 6 in accordance with the intensity of light due to a photovoltaic effect. The intensity of light generated by the chemiluminescent reaction depends on the quantity of a reactive substance in the that sample that reacts with the chemiluminescent reagent. Therefore, the quantity of the reactive substance can be determined from the current flowing through the ammeter 6. In other words, a quantitative analysis can be made by the detector. If a reagent which reacts only with the specific substance is selected as the chemiluminescent reagent, it becomes possible to know whether or not the specific substance is contained in the test sample. In order words, qualitative analysis can also be made by the detector.

FIG. 2 is a drawing depicting an example of the definite structure of the chemiluminescent detector of the present invention. The chemiluminescent detector has a three-layered structure formed by sandwiching a silicon single crystal substrate 9 between two glass substrates 8. A sample introduction port 10 and a chemiluminescent reagent introduction port 11 are disposed on the silicon single crystal substrate 9. A plurality of through-holes 12 are formed in the silicon single crystal substrate 9, and are connected with one another by very small grooves in such a manner as to define one flow passage and to constitute a reaction unit 13. A photodiode structure is fabricated on the silicon single crystal substrate 9 to form the detection unit 14.

Next, FIGS. 4A to 4C show an example where the chemiluminescent detector of the present invention is applied to the analysis of amino acids using liquid chromatography. After an amino acid (Dns-AA) which is in advance subjected to a dansyl method is separated by a column, it is reacted with bis-2,4,6-trichlorophenyloxalic acid and hydrogen peroxide (FIGS. 4A and 4B to generate dansylamino acid (Dns-AA*)in the excitation state. Light is emitted by this Dns-AA* when it returns to Dns-AA in ground state (FIG. 4C) and the light is detected. In comparison with the conventional apparatus, the chemiluminescent detector of the present invention can make measurement using a much smaller quantity of the test sample and since the distance of the detection unit from the reaction unit is shorter, attenuation of luminescence does not occur much and measurement can be carried out with high sensitivity.

When the chemiluminescent detector of the present invention is used, measurement can be carried out with higher sensitivity using a smaller quantity of the test sample than by the conventional apparatus.

What is claimed is:

1. A chemiluminescent detector for detecting a specific substance contained in a test liquid by a chemiluminescent reaction, comprising:
    a reaction unit for inducing a chemiluminescent reaction by mixing a test sample with a chemiluminescent reagent;
    a detection unit for detecting chemiluminescent light comprising a photosensor; and
    means including a first introduction port for introducing the test sample and a second introduction port for introducing the chemiluminescent reagent into the reaction unit; p1 wherein both of said reaction unit and said detection unit are formed in and integral with a common substrate.

2. A chemiluminescent detector according to claim 1; wherein said substrate is a single crystal silicon plate.

3. A chemiluminescent detector according to claim 1; wherein said substrate is sandwiched between two glass plates.

4. A chemiluminescent detector according to claim 2; wherein said reaction unit is fabricated by anisotropic etching in said substrate.

5. A chemiluminescent detector according to claim 4; wherein said reaction unit has a plurality of through-holes formed in the substrate and interconnected by at least one groove formed in the substrate.

6. A chemiluminescent detector according to claim 2; wherein said detection unit comprises a silicon photodiode fabricated on said substrate.

7. A chemiluminescent detector, comprising: a substrate; a reaction unit formed in and integral with the substrate for mixing a test sample with a chemiluminescent reagent; a detection unit having a photosensor formed in and integral with the substrate for detecting chemiluminescent light generated by a chemiluminescent reaction between the test sample and the chemiluminescent reagent; and introducing means for introducing the test sample and the chemiluminescent reagent into the reaction unit.

8. A chemiluminescent detector according to claim 7; wherein the substrate comprises a single crystal silicon plate.

9. A chemiluminescent detector according to claim 8; wherein the reaction unit has a plurality of through-holes anisotropically etched in the substrate and interconnected by at least one groove anisotropically etched in the substrate.

10. A chemiluminescent detector according to claim 7; further comprising a pair of glass plates sandwiching the substrate.

11. A chemiluminescent detector according to claim 7; wherein the reaction unit has a plurality of through-holes extending through the substrate and interconnected by at least one groove in the substrate.

12. A chemiluminescent detector according to claim 7; wherein the detection unit comprises a silicon photodiode.

13. A chemiluminescent detector, comprising: a single crystal silicon substrate; a reaction unit for mixing a test sample with a chemiluminescent reagent, the reaction unit being formed in and integral with the substrate and having a plurality of through-holes extending through the substrate and interconnected with at least one groove formed in the substrate; a detection unit including a silicon photodetector formed in and integral with the substrate for detecting chemiluminescent light generated by a chemiluminescent reaction between the test sample and the chemiluminescent reagent; and introducing means for introducing the test sample and the chemiluminescent reagent into the reaction unit.

14. A chemiluminescent detector according to claim 13; further comprising a pair of glass plates sandwiching the substrate.

* * * * *